United States Patent [19]

Payton et al.

[11] Patent Number: 4,742,824
[45] Date of Patent: May 10, 1988

[54] OXYGEN TUBE SUPPORT PATCH

[75] Inventors: Hugh W. Payton, 36 S. Main St., Jeffersonville, Ohio 43128; Harold G. Wyse, Dayton, Ohio

[73] Assignee: Hugh W. Payton, Washington Court House, Ohio

[21] Appl. No.: 932,232

[22] Filed: Nov. 19, 1986

[51] Int. Cl.⁴ .............................................. A61M 15/08
[52] U.S. Cl. ........................ 128/207.18; 128/DIG. 26; 604/174
[58] Field of Search .......... 128/DIG. 26, 912, 207.13, 128/207.18, 203.22, 203.23, 206.11; 604/177, 180, 94, 174; 235/90

[56] References Cited

U.S. PATENT DOCUMENTS

| 40,999 | 12/1863 | Gill | 235/90 |
|---|---|---|---|
| 2,402,306 | 6/1946 | Turkel | 128/215 |
| 2,590,006 | 3/1952 | Gordon | 128/206 |
| 3,046,984 | 7/1962 | Eby | 128/214 |
| 3,288,136 | 11/1966 | Lund | 128/133 |
| 3,630,195 | 12/1971 | Santomieri | 128/133 |
| 3,782,388 | 1/1974 | Page | 128/348 |
| 4,025,015 | 5/1977 | Kolic | 248/205 |
| 4,122,857 | 10/1978 | Haerr | 128/348 |
| 4,129,128 | 12/1978 | McFarlane | 128/133 |
| 4,170,995 | 10/1979 | Levine et al. | 128/346 |
| 4,209,020 | 6/1980 | Nielsen | 128/640 |
| 4,224,937 | 9/1980 | Gordon | 128/133 |
| 4,435,175 | 3/1984 | Friden | 604/177 |
| 4,659,329 | 4/1987 | Annis | 128/DIG. 26 |
| 4,660,555 | 4/1987 | Payton | 128/DIG. 26 |

FOREIGN PATENT DOCUMENTS

WO86/06640 11/1986 PCT Int'l Appl. ................. 604/180
1471609 4/1977 United Kingdom ....... 128/DIG. 26

Primary Examiner—Kyle L. Howell
Assistant Examiner—Timothy G. Philips
Attorney, Agent, or Firm—Biebel, French & Nauman

[57] ABSTRACT

An adhesive face patch for the support of an oxygen tube for the purpose of supplying supplemental oxygen to a patient includes a body formed generally in the shape of a three-leaf clover with petals which are bendable with respect to each other at a central section to conform to a patient's cheek contour at the maxillary prominence, includes tube-receiving pedestals or posts formed in pairs on lateral petals to receive an oxygen tube and to cause the tube be held in a curved state to redirect the tube to or toward the nostril, and a center pedestal over which the tube may be looped after adjusting for comfort, so that the oxygen tube may have a slight upward thrust to assist in supporting the nasal insert and retaining the same in place.

4 Claims, 1 Drawing Sheet

U.S. Patent   May 10, 1988   4,742,824
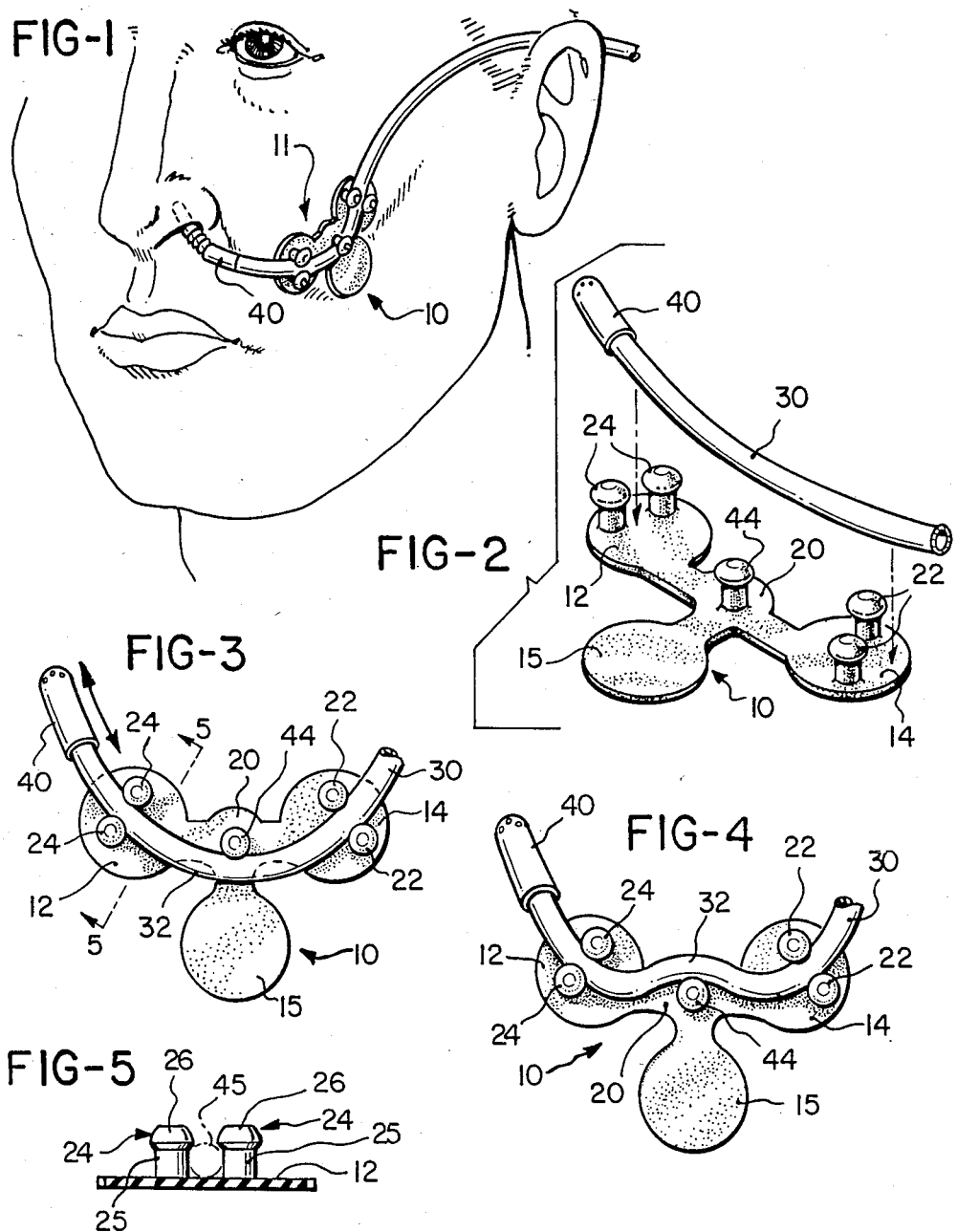

OXYGEN TUBE SUPPORT PATCH

BACKGROUND OF THE INVENTION

In co-pending application, Ser. No. 798,159 filed Nov. 15, 1985, now U.S. Pat. No. 4,660,555 issued Apr. 28, 1987, there is disclosed an improved unilateral system for supplying supplemental oxygen to a patient. That application also discloses an improved oxygen tube holder which has a base of arcuate shape adapted to be mounted on a support patch and in which the support has a central retaining electrode or button. The holder of that application preformed the oxygen tube into a curved configuration, between pairs of tube grippers or holding fingers.

The particular tube holder as disclosed in the pending application has not been entirely satisfactory in clinical tests. The curved tube holder, mounted on a metal button or electrode of a skin patch, at times provided insufficient support for the tube and permitted the nosepiece to drop free. Further, its placement and use was sometimes found to be awkward, and as a disposable item, its cost was relatively high by reason of the two-part construction. The holder did not provide ease of adjustment of the oxygen tube after insertion into the tube supports.

Accordingly, there is still a need for an improved oxygen tube holding patch which is easy to use, which permits ease of axial and rotational adjustment of the oxygen tube after the patch has been placed on the patient's face, which supports the tube with an upward thrust toward the nasal cavity, and which is low cost and universally applicable.

SUMMARY OF THE INVENTION

The present application is directed to an improved low cost yet highly versatile face patch for the selective support of an oxygen tube, such as for the application of supplemental oxygen to a patient. The particular patch is characterized by versatility and an ability to provide for lateral adjusting movement of the tube when adjustment is required, and thereafter permitting the tube to be locked or clamped into a preadjusted position. This is accomplished by the employment of a substrate body which is formed generally in the shape of a three-leaf clover having a front petal, a back petal, and a bottom petal, all joined at a common central section. Stated in other terms, the patch will utilize three circle-shaped portions joined in a three-leaf clover pattern, with each of the circles joined by a slender isthmus which allows each of the three petals making up the patch to be bent or conformed, so as to be contoured to any variance in the maxillary prominence. The base is provided with sufficient thickness for support of the posts thereon, forming a part of the patch.

Each of the front and back petals is provided with a pair of tube-receiving pedestals or posts which are proportioned to receive the oxygen tube therebetween. The posts are formed with enlarged ends or tips to prevent accidental dislodgment of the tube from the spaces therebetween. The paired lateral posts are spaced so as to allow the oxygen delivery tube to be inserted therebetween.

The arrangement assures that the oxygen tube will not be dislodged, and yet may be adjusted to and fro in the longitudinal axial of the tube and also rotated with ease. Thus, two pairs of posts are provided on the remote petals. A fifth post is positioned in the general area of the junction of the center petal with the connecting isthmus and is clear of the tube during adjustments of the location and position of the tube, as noted above. The fifth post also forms a locking post over which an intermediate section of the oxygen tube may be looped to lock the tube in a preadjusted position. When locked, the tube may be caused to provide a continuous stable upward thrust of the nasal insert piece. The upward thrust assures that the nasal insert will not gradually fall away from the nostril and progressively compromise the desired oxygen delivery.

When the patch is located on the face, the center or downwardly directed petal projects away from the cheek and away from the oribital rim. The position of this petal with respect to the other two petals and the body of the patch may be adjusted or preformed to conform to the cheek contour.

It is accordingly an important object of this invention to provide a patch for supporting an oxygen tube which is highly versatile in application, low in cost, and easy to apply.

A further object of the invention is the provision of a patch for supporting an oxygen tube, for delivering supplemental oxygen to a patient, in which the tube may be caused to be urged through an angle upwardly in such a manner that the nasal insert is urged into its seated or operative invention.

A still further object of the invention is the provision of an oxygen tube support patch, having a configuration generally that of a three-leaf clover, in which two of the uppermost petals and a center portion are formed with oxygen support posts, and in which a bottom or third petal provides support or stability to the patch.

A still further object of the invention is the provision of an oxygen tube support patch, in which the tube in one position may be freely adjusted with respect to laterally spaced support posts on the patch, and in a second position supports or locks the tube in place.

These and other objects and advantages of the invention will be apparent from the following description, the accompanying drawings, and the appended claims.

BRIEF DESCRIPTION OF THE DRAWINGS

FIG. 1 is a pictorial view showing the use of the oxygen tube support patch of this invention;

FIG. 2 is a perspective view of the patch showing an oxygen tube prior to placement thereon;

FIG. 3 is a plan view of the patch, showing the oxygen tube in the unlatched adjustable position;

FIG. 4 is a view similar to FIG. 3 but showing the oxygen tube in the latched or adjusted position; and FIG. 5 is a transverse section along the line 5—5 of FIG. 3.

DESCRIPTION OF THE PREFERRED EMBODIMENT

Referring to the figures of the drawing which illustrate a preferred embodiment of the invention, an improved adhesive face patch for the selective support of an oxygen tube, such as for the application of supplemental oxygen to a patient, is illustrated generally at 10 in FIGS. 1 and 2. The patch 10 is formed with a generally planar and pliable body formed of plastic material, such as medical grade vinyl, and is provided with a medical grade adhesive material on its under or backside, such as for securing the patch to the maxillary prominence region 11 of the face, as shown in FIG. 1.

The patch 10 is formed with a body generally in the shape of a three-leaf clover, including a front petal 12, a back petal 14, and a bottom petal 15 joined to each other at a generally common central section 20. The central section 20 is of reduced as compared to the maximum width of each of the petals.

Each of the front and back petals 12 and 14 has a pair of identical tube-receiving pedestals or posts thereon. The back petal has a pair of upstanding posts 22 while the front petal 14 has a similar pair of upstanding posts 24, extending upwardly from the planar upper surface of the patch. Each of the pedestals is formed with a cylindrical body 25 terminating in a slightly enlarged head 26, as shown in FIG. 5. The pedestal pairs are proportioned to receive an oxygen tube 30 therebetween, accompanied by a slight spreading apart of the heads 26. The bodies 25 of each such pair are spaced apart a distance about equal to the distance of the oxygen tube 30, shown in phantom in FIG. 5. When the tube 30 is inserted, it is retained by the heads 26 in the spaces between the pairs of posts against accidental dislodgement, but the tube may be freely rotated on its axis, and may be positioned longitudinally.

It will be seen in FIG. 3 that the pair of posts 22 are set at an angle to the pair of posts 24, such as an approximate 60° angle, so that the tube 30 enters the first pair 22 with a downward inclination and exits the second pair 24 with an upward inclination, with an intermediate section 32 of the tube curved therebetween. The posts are thus so arranged so as to divert the oxygen tube 30 through an angle from its downward run into the patch from a rearward position with respect to the patient's head, to a somewhat upward direction, toward the nasal cavity. As shown in FIGS. 2 and 3, the tube 30 may terminate in an oxygen administering plug or nasal insert 40, which insert may be made in accordance with the teachings of the co-pending application, as identified above.

Thus, it is intended that the tube 30 enter with a downward inclination and exit with an upward inclination. The height of the post heads above the patch planar surface need not exceed the diameter of the tube.

The invention further includes provision by which the tube 30 may be locked in a preadjusted position, such as to provide a continuous and stable upward thrust of the insert 40, to prevent the same from gradually falling away from the nostril. This is accomplished by a fifth or central pedestal or post 44, located in the common central section 20, and positioned immediately above the relaxed position of the tube thereon, as shown in FIG. 3. The post 44 forms means over which the portion 32 of the tube may be looped as shown in FIG. 4, for locking the tube 30 in a preadjusted position on the patch 10.

When the tube is in the relaxed position shown in FIGS. 1 and 3, the oxygen tube may be adjusted both longitudinally and rotationally, to assist in the adjustment of the nasal tip or insert 40 in a comfortable position. Once the insert 40 is comfortable, the tube can then be locked in position simply by lifting the portion 32 thereof from its relaxed position below the post 44 and looping the same above the post 44 as shown in FIG. 4.

It is preferred to position the patch on the face substantially as shown in FIG. 1, with the downwardly depending petal 15 extending away from the eye and downwardly on the cheek. This petal may be conformed or bent slightly with respect to the center section, as may be the petals 12 and 14, to cause the patch to conform gently to the skin surface. If desired, the petal 15 may be preformed with an inward inclination so as to conform to the contour of the fall off of the lower cheek toward the jaw.

In a preferred embodiment, without intending to limit the scope of the invention, the maximum width of the patch may be in the order of 3.5 cm, and the individual petals may have a width in the order of 1.0 cm. The height of the patch, from top to bottom may be in the order of 2.0 cm. The pedestals or posts may extend above the surface in the order 0.675 cm with a spacing therebetween of 0.3 cm at the bodies 25 to receive a 0.3 mm diameter tube therebetween. While the invention is particularly adapted for use at the cheek prominence, a second patch may be attached substantially at the mastoid prominence, providing a second support of a tube 30, where desirable.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. An improved adhesive face patch arrangement for the selective support of an oxygen tube for the application of supplemental oxygen to a patient, comprising:

a patch having a body formed of pliable plastic sheet material generally in the shape of a three-leaf clover having a front petal, a back petal and a bottom petal joined to each other at a central common section of a substantially narrower width compared to the maximum width of each of said petals, said petals being bendable with respect to each other about said central section to conform to a patient's face contour, and being proportioned to be received on a patient's cheek bone prominence, a flexible oxygen delivery tube, each of said front and back petals having a pair of tube-receiving pedestals proportioned to receive said oxygen tube therebetween and said pair on said front petal set at an angle to said pair on said back petal so that said tube enters one said pair with a downward inclination toward said bottom petal and exits the other said pair with an upward inclination away from said bottom petal defining a relaxed position of said tube, a single said pedestal on said central common section positioned above said relaxed position of said tube thereon and forming a post over which a portion of the tube at said central common section may be looped for locking said tube in a preadjusted position on said patch, and medical grade adhesive on said body on the side thereof remote from said pedestals.

2. The patch of claim 1 in which said pedestals are formed with enlarged ends which prevent accidental dislodgement of said tube therefrom while providing for longitudinal and rotational adjustment therebetween.

3. An improved adhesive patch arrangement for the support of a flexible tube extending therefrom to the nostril of a patient, comprising:

a patch having a support body of medical grade vinyl sheet material, medical grade adhesive on one side of said body for conforming attachment of said patch in the general region of the patient's cheek bone prominence, a flexible tube, a plurality of upstanding posts on said body extending from the other side thereof, each said post having an enlarged head on the end thereof including a first pair of said posts in spaced-apart relation and adapted to receive said tube therebetween by slight deflections of said heads during tube insertion and thereafter tending to retain said tube adjacent said body, a second said pair of said posts on said body spaced from and at an angle to said first pair of posts to cause an intermediate section of said tube to curve with said tube entering said patch with a downward inclination with respect to said patient's face and exiting said patch with an upward inclination, and a fifth said post on said body intermediate said first and second pairs of posts and above said intermediate tube section curvature and adapted to engage said tube by the lifting of said intermediate tube section thereabove for locking said tube in adjusted position on said patch.

4. The patch of claim 3 in which said patch body is shaped in the form of a three-leaf clover having a front petal, a back petal and an intermediate downwardly-extending petal, each of said petals being joined at a common central section, and which said first and second posts pairs are located respectively on said front and back petals, and in which said fifth post is located on said body central section.

* * * * *